(12) United States Patent
Fang et al.

(10) Patent No.: US 11,254,636 B2
(45) Date of Patent: Feb. 22, 2022

(54) ETHYL ACETATE REMOVAL DURING VAM PRODUCTION

(71) Applicant: LyondellBasell Acetyls, LLC, Houston, TX (US)

(72) Inventors: Linn Fang, Houston, TX (US); Chuc T. Nguyen, La Porte, TX (US)

(73) Assignee: LyondellBasell Acetyls, LLC, Houston, TX (US)

( * ) Notice: Subject to any disclaimer, the term of this patent is extended or adjusted under 35 U.S.C. 154(b) by 0 days.

(21) Appl. No.: 16/984,975

(22) Filed: Aug. 4, 2020

(65) Prior Publication Data

US 2021/0040027 A1 Feb. 11, 2021

Related U.S. Application Data

(60) Provisional application No. 62/882,911, filed on Aug. 5, 2019.

(51) Int. Cl.
*C07C 67/54* (2006.01)
*B01D 3/42* (2006.01)
*C07C 69/15* (2006.01)

(52) U.S. Cl.
CPC ............ *C07C 67/54* (2013.01); *B01D 3/4238* (2013.01); *C07C 69/15* (2013.01)

(58) Field of Classification Search
CPC ....... C07C 67/54; C07C 69/003; C07C 69/15; B01D 3/143; B01D 3/4238
See application file for complete search history.

(56) References Cited

U.S. PATENT DOCUMENTS

| 4,934,519 A | 6/1990 | Wolf et al. |
| 6,228,226 B1 | 5/2001 | Hess et al. |

FOREIGN PATENT DOCUMENTS

| EP | 0992483 A1 * | 4/2000 | ............. C07C 67/54 |
| GB | 1271104 A * | 4/1972 | ............... B01D 3/36 |

OTHER PUBLICATIONS

The International Search Report and The Written Opinion for PCT/US2020/044893 dated Dec. 15, 2020.

* cited by examiner

*Primary Examiner* — Yate' K Cutliff

(57) ABSTRACT

Purification methods and systems for working up a crude vinyl acetate stream containing vinyl acetate monomer, acetic acid, water, ethyl acetate, and other impurities. Crude vinyl acetate streams are purified with an azeotropic distillation tower using a side draw to remove ethyl acetate and water, and a bottom stream to remove acetic acid from the crude vinyl acetate. The methods and systems move the side draw to a location on the azeotropic distillation tower that maintains a constant water concentration in the bottom product of about 4 to about 15 wt. % and forms a vapor side product. A second distillation tower is used to further purify the vapor side product to obtain water, VAM, ethyl acetate and AA. The system provides easier disposal of ethyl acetate, and cleaner water that can be recycled in the reactor or purification sections of a VAM plant and full recovery of AA.

7 Claims, 2 Drawing Sheets

ETHYL ACETATE REMOVAL DURING VAM PRODUCTION

PRIOR RELATED APPLICATIONS

This application claims the benefit of priority to U.S. Provisional Application No. 62/882,911 filed Aug. 5, 2019, which is incorporated here by reference in its entirety.

FEDERALLY SPONSORED RESEARCH STATEMENT

Not applicable.

REFERENCE TO MICROFICHE APPENDIX

Not applicable.

FIELD OF THE DISCLOSURE

The disclosure relates to vinyl acetate monomer production, particularly to systems and methods for purifying crude vinyl acetate monomer streams.

BACKGROUND OF THE DISCLOSURE

Vinyl acetate monomer (VAM) is a intermediate in the synthesis of a number of polymers and resins for adhesives, coatings, paints, films, textiles and other end products. A common derivative is polyvinyl acetate (PVA), which is mainly used as an adhesive because it has good adhesion properties for porous materials and can be used with a number of substrates including paper, wood, plastic films and metals. Other uses for PVA include paper coatings, paints and industrial coatings. A fast-growing use of VAM is in the manufacture of ethylene vinyl alcohol (EVOH), which is used as a barrier resin in food packaging, plastic bottles, and gasoline tanks, and in engineering polymers. Because of VAM's broad uses, vinyl acetate-derived polymers are used in many manufactured products.

A common industrial process to produce VAM is a vapor-phase acetoxylation of ethylene that is carried out in a fixed-bed tubular reactor. During this vapor-phase acetoxylation, VAM is synthesized in the acetoxylation reactor by reacting an excess of acetic acid, oxygen, and ethylene in the presence of an alumina- or silica-supported palladium catalyst in conjunction with gold along with an alkali metal salt. The gaseous stream exiting the acetoxylation reactor contains ethylene, oxygen, carbon dioxide, vinyl acetate monomer, acetic acid, water, ethyl acetate, and other impurities. This gaseous stream is partially condensed and/or scrubbed with acetic acid and/or water and the uncondensed portion is processed to recover ethylene and oxygen for recycling back to the acetoxylation step for additional VAM production. Unreacted acetic acid is recovered by distillation before being recycled back to the acetoxylation reactor for additional yield of VAM.

The condensed stream is the crude VAM stream, which includes VAM, acetic acid, water, ethyl acetate, and other reaction products. This crude stream can be purified by an azeotropic distillation, between VAM and water, in the purification section of the VAM plant. During distillation, a VAM enriched vapor stream is obtained as an overhead product, an acetic acid rich liquid stream is obtained as a bottom product, and, in modern systems, an ethyl acetate enriched liquid stream is obtained as a side stream. The bottom product is recycled to the acetoxylation reactor for further VAM production, while the side stream is a liquid stream that undergoes further fractionation to remove impurities such as ethyl acetate or to be disposed.

While the overhead product exiting the azeotropic distillation tower is enriched with VAM, undesirable components are also present, particularly water and ethyl acetate. The overhead product is condensed and further separated into an organic phase containing VAM, a water phase that is partially taken as a reflux stream for the azeotropic distillation, with the rest of the water undergoing further processing to form a cleaner water stream for disposal. The organic phase is the enriched VAM stream that is further distilled to remove undesirable components such as water and ethyl acetate, among others. However, due to similar boiling behavior of vinyl acetate and ethyl acetate, separation of the ethyl acetate requires a high energy consumption and is costly. As such, a significant fraction of this portion of ethyl acetate is left in the finished VAM product according to a given product quality specification.

Many improvements have been made to the distillation and VAM purification process to reduce the amount of ethyl acetate remaining the in VAM product to meet predetermined specification (about 250 ppm by weight). However, there exists a need for improving the purification process to further reduce the amount of ethyl acetate in the finished VAM product while improving the overall VAM production efficiency. Although current VAM processes are successful in achieving an acceptable product, even incremental improvements in technology can mean the difference between a cost-effective purification process, and cost prohibited energy and production losses.

SUMMARY OF THE DISCLOSURE

The present disclosure provides improved methods and systems for purifying a crude vinyl acetate monomer (VAM) stream. The improved methods and systems provide for inexpensive changes to the azeotropic distillation tower, while adding a second distillation tower to the purification section of the VAM production site to increase the amount of ethyl acetate (ETAC) being removed from the crude VAM stream. Specifically, the side stream on the azeotropic distillation tower is moved to a location on the tower to obtain a constant concentration of 4 to 15% water in the bottom product of the azeotropic distillation tower, which results in an ethyl acetate enriched vapor stream as the side stream. The second distillation tower has been added to treat the side vapor stream to obtain additional acetic acid and water for recycling back into the VAM production process.

The VAM purification process equipment has two outlets for ethyl acetate: the side stream and the overhead product of the azeotropic distillation tower. As some VAM is mixed with the ethyl acetate in both outlets, the improved methods and systems described here increase the ratio of ethyl acetate to VAM in the side stream but decreases the ratio of ethyl acetate to VAM in the overhead stream. This will reduce the amount of ethyl acetate that is carried over into the downstream VAM finishing processes while also increasing the amount of VAM that is ultimately recovered from the crude VAM stream through the overhead product.

Further improvements to the VAM purification process include generation of better-quality fuel streams for combustion in other areas of the plant and cleaner water streams that do not need extensive treatment before being recycled or disposed. This results in an improved overall water balance of the VAM production process and reduced energy cost of the purification process.

The present system includes any of the following embodiments, in any combination(s) of one or more thereof:

A method for purifying a crude liquid vinyl acetate feed comprising feeding a crude liquid vinyl acetate stream from a vinyl acetate monomer reactor into a distillation tower and distilling the crude liquid vinyl acetate stream, wherein the crude liquid vinyl acetate stream has vinyl acetate monomers, acetic acid, water, and ethyl acetate. A vapor product that is predominantly a water and vinyl acetate monomer azeotrope mixture is removed from the top of the distillation tower; a liquid product comprising water and acetic acid is removed from the bottom of the distillation tower; and, a vapor side stream comprising acetic acid, water, vinyl acetate monomer and ethyl acetate is removed from the side of the distillation tower. The vapor side stream can be fed into a second distillation tower and distilled. Following distillation in the second distillation tower, acetic acid and a portion of water are removed from the bottom of the second distillation tower as a liquid product, while the vinyl acetate monomer, the ethyl acetate and the remaining portion of water are removed from the top of the second distillation tower as a vapor product. After condensing, the top product from the second distillation tower is separated into a vapor stream, an aqueous stream and an optional organic stream. A portion of the aqueous stream is returned to the second distillation tower as reflux and a second portion of the aqueous stream is sent to a water treatment plant or a reaction area of the vinyl acetate monomer reactor.

Any of the methods above, further comprising condensing and decanting the vapor stream exiting the separator connected to the second distillation tower to form an aqueous stream and an organic stream, wherein the organic stream is incinerated and the aqueous stream is sent to a water treatment plant or a reaction area of the vinyl acetate monomer reactor.

Any of the methods above, wherein the liquid product from the first distillation tower has a constant water concentration of about 4 to 15 wt. %. Alternatively, this liquid product has a constant water concentration of about 9 to 11 wt. %.

Any of the methods above, further comprising incinerating the vapor stream and the optional organic phase exiting the separator on the second distillation tower.

Any of the methods above, further wherein the first distillation tower contains 50 to 90 trays and is operated under 1 to 5 bars of absolute pressure.

Any of the methods above, further wherein the feed inlet tray of the first distillation tower is located between the middle section of the tower and the top of the tower.

Any of the methods above, wherein condensing of the vapor product of the second distillation tower occurs in a temperature range of about 35 to about 105° C.

Any of the methods above, wherein an optional organic stream is produced from the vapor product of the second distillation when the temperature range of condensation step for top product from the second distillation tower is about 35 to about 78° C.

A system for purifying a crude liquid vinyl acetate feed comprising a first and second distillation tower. The first distillation tower has a crude liquid vinyl acetate feed inlet for introducing the product from a vinyl acetate monomer reactor, wherein this inlet is located between the middle section and the top of the distillation tower. At the top of the first distillation is an outlet for releasing a first vapor product that is predominantly a water and vinyl acetate azeotrope mixture. This vapor product is condensed and separated into a first aqueous stream, a first organic stream, and a first gas stream. At the bottom of the first distillation is an outlet for releasing a liquid product comprising water and acetic acid, wherein liquid product is recycled to a vinyl acetate monomer reactor or reaction area of vinyl acetate monomer reactor. The first distillation tower also has a side outlet for removal of a side vapor product comprising acetic acid, water, vinyl acetate and ethyl acetate. This side vapor product can be fed into an inlet on a second distillation tower and distilled. At the bottom of the second distillation tower is an outlet for removal of a liquid product comprising acetic acid and water, wherein this liquid product is recycled to a vinyl acetate monomer reactor or reaction area of vinyl acetate monomer reactor. At the top of the second distillation tower is an outlet for the removal of a second vapor product that comprises vinyl acetate monomer, ethyl acetate, and water. The second vapor product is condensed and separated into a second aqueous stream, a second gas stream, and an optional second organic stream. The operational temperature of the condenser for the second vapor product affects the purity of the aqueous stream and/or the presence of the optional second organic stream.

Any of the above systems, wherein the crude liquid vinyl acetate feed comprises vinyl acetate, acetic acid, water, and ethyl acetate.

Any of the above systems, wherein the first aqueous stream comprises vinyl acetate monomer, water and minor amounts of ethyl acetate; the organic stream comprises vinyl acetate monomer and water; and, the first gas stream comprises vinyl acetate monomer and water.

Any of the above systems, wherein the liquid product of the first distillation tower has a constant water concentration of about 4 to 15 wt. %.

Any of the above systems, wherein a partial amount of the first organic stream is recycled to the first distillation tower as a reflux.

Any of the above systems, wherein the reflux has a ratio of vinyl acetate monomer recycled to vinyl acetate monomer removed between 2.0 to 4.5.

Any of the above systems, wherein the second aqueous stream comprises vinyl acetate monomer, water and minor amounts of ethyl acetate; the optional second organic stream comprises vinyl acetate monomer, ethyl acetate and minor amounts of water; and, the second gas stream comprises vinyl acetate monomer, ethyl acetate, and water.

Any of the above systems, wherein the first distillation tower contains 50 to 90 trays and is operated under 1 to 5 bars of absolute pressure.

Any of the above systems, wherein the operational pressure of the second distillation tower is slightly below the pressure of the side outlet in the first distillation tower.

Any of the above systems, wherein the second aqueous stream has a high water purity and is recycled to the vinyl acetate reactor when the second condenser and phase separator are operated at temperatures between about 79 to about 120° C.

Any of the above systems, wherein the second aqueous stream has a low water purity and is recycled as a reflux stream to the second distillation tower when the second condenser and phase separator are operated at temperatures between about 30 to about 78° C.

Any of the above methods or systems, further comprising a third condenser and phase separator fluidly connected to the second condenser and phase separator, wherein the third condenser and phase separator further condense and purify the second gas stream.

Any of the above systems, wherein the optional second organic stream is present when the condensing occurs in a temperature range of about 35 to about 78° C.

DEFINITIONS

Figure 1:
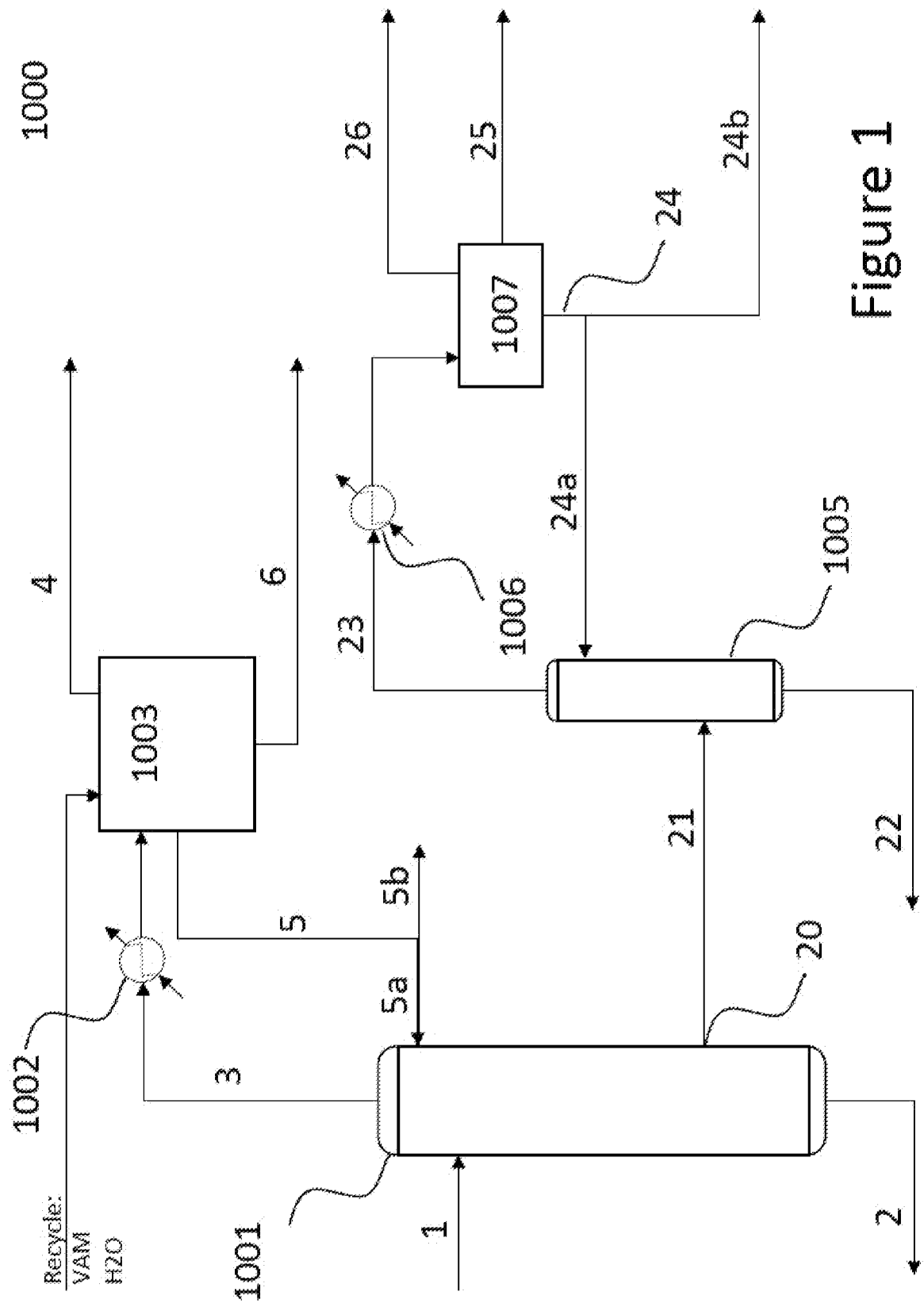
FIG. 1. Schematic of one embodiment of the disclosed improved crude VAM purification process that utilizes a second distillation tower to treat an ethyl acetate enriched vapor side stream.

As used herein, the terms "crude vinyl acetate monomer stream" or "crude vinyl acetate stream" or "crude VAM stream" are used interchangeably to refer to the stream exiting the VAM reactor after unreacted ethylene and unreacted oxygen are removed. This crude stream contains VAM, acetic acid, water, ethyl acetate, and other impurities. As an example, the crude vinyl acetate stream can comprise, by weight, about 10 to 20% of VAM, about 3 to 15% of water, about 0.01 to 0.2% of ethyl acetate, less than 0.5% of impurities such as diacetate, polymers, acetaldehyde and the like, with acetic acid comprising the remaining amount to reach 100% by weight.

The term "distillation tower" refers to a tower that is capable of separating a mixture into its component parts or fractions by selective boiling and condensing. In a simple distillation scheme, the mixture is fed into a tower with heat provided at the bottom of the tower, wherein the resulting vapor rises through the tower, contacting the liquid on the trays, before exiting the tower at the top. The exiting vapor can be partially or entirely condensed in a condenser attached to the top of the distillation tower. A portion or all of the liquid condensate flows back into the tower as a reflux that travels downward through the trays counter current to the rising vapor, and while being held on trays, in contact with the rising vapor. The reflux eventually reaches the bottom of the tower. The more reflux and/or more trays provided, the better the tower's separation of lower boiling materials from higher boiling materials. In some towers, packing materials can be used in place of trays. For simplicity, the distillation towers herein reference the number of trays, but it should be understood that an equivalent amount of packing can also be used in place of trays. The trays are labeled from top to bottom.

The terms "azeotropic tower" or "azeotropic distillation tower" refer to the primary distillation tower where a majority of the VAM is isolated and recovered from the crude vinyl acetate stream as a predominantly water-VAM azeotropic mixture.

The terms "ETAC tower" and "ethyl acetate tower" refers to the secondary distillation tower that separates components in the vapor side stream exiting the primary distillation tower.

The terms "side draw stream", "side vapor product" and "side vapor stream" are used interchangeably to refer to the stream exiting the azeotropic distillation tower (or 'first' distillation tower) and being introduced into the ETAC tower (or 'second' distillation tower).

As used herein, the terms "undesirable component" or "undesirable components" refer to component(s) in the enriched VAM stream that are not desired in the finished VAM product or whose concentration in the finished VAM product must be reduced to meet predetermined specifications. These components can include, but are not limited to, both unreacted starting materials and reaction products of the vapor-phase acetoxylation process. The "enriched VAM stream" is the distillation product stream removed from the top of the azeotropic distillation tower.

The term "trace", in reference to concentrations in the various separation streams, refers to amounts in the range of greater than 0.0005 wt. % but less than 0.02 wt. %. The term "minor", in reference to concentrations in the various separation streams, refers to amounts in the range of 0.02 wt. % to less than 1.0 wt. %.

The term "high purity", in reference to water, refers to a stream having about 99 wt. % or greater of water. The term "low purity", in reference to water, refers to a stream having less than 99 wt. % of water.

As used herein, the "reaction area" refers to a physical area within a VAM production plant where the vapor phase acetoxylation takes place in a reactor or reactors, and where VAM, water and unconverted AA (among other components) in the reactor effluent are condensed to form a crude VAM stream. The uncondensed gas, containing e.g. ethylene, oxygen and carbon dioxide, is processed to remove undesirable components before being recycled to the inlet of the reactor(s). In some embodiments of the present system, the non-VAM streams can be recycled to the reaction area for use in e.g. scrubbing of streams exiting the reactors. In some embodiments of the present system, a portion of the non-VAM streams can be recycled to the reaction area (e.g., for use in scrubbing) with the balance returning to the reactor.

As used herein, the term "combusted" is broadly defined as processes of chemically or physically changing a material to produce light and/or heat. It can refer to incineration, flaring, or use of the material as a liquid fuel to generate steam. Combusting the material as a liquid fuel may reduce cost on-site, whereas incineration or flaring may provide no value. However, the quality of the material stream dictates the form of combustion that is selected (e.g. a material stream that is not energy efficient for fuel purposes would likely be incinerated or flared).

All concentrations herein are by weight percent ("wt. %") unless otherwise specified.

The term "slightly below" in reference to the operational pressure of the second distillation tower means the stated pressure of the side outlet of the azeotropic distillation tower minus up to 10%.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
| --- | --- |
| ETAC | ethyl acetate |
| AA | acetic acid |
| VAM | vinyl acetate monomer |
| psig | pounds per square inch, gage |
| wt. % | Percent in weight |

Description of Embodiments of the Disclosure

The present disclosure provides improved systems for removing ethyl acetate (ETAC) from a crude vinyl acetate monomer (VAM) stream. Specifically, the side draw on the primary azeotropic distillation tower is moved to a location on the tower that results in the azeotropic distillation tower's bottom product having an amount of water that is constantly between 4 and 15 wt. %. By placing the side draw based on a constant amount of water in the bottom product, the side draw stream becomes a vapor and there is an increase in the amount of ETAC in the ETAC-enriched vapor stream exiting the tower during the distillation process, resulting in an increase in the ratio of ETAC to VAM in the side vapor stream. This ETAC-enriched vapor stream can then undergo further distillation processes in a newly added second distillation tower to further separate out the ETAC for disposal, and recover additional water and acetic acid for recycling in the VAM production process. The overhead product exiting the azeotropic distillation tower has a smaller amount of ETAC present (e.g. decreased ETAC to VAM ratio), which reduces the amount VAM that will be lost during the purification of the overhead product, and improve the quality of the finished VAM product.

Removal of ETAC using the presently disclosed systems results in a more economically advantageous VAM purification process while decreasing consumption of energy and water, and/or decreasing loss of VAM in the ETAC-enriched side stream. Methods of using the improved systems are also described.

Figure 2:
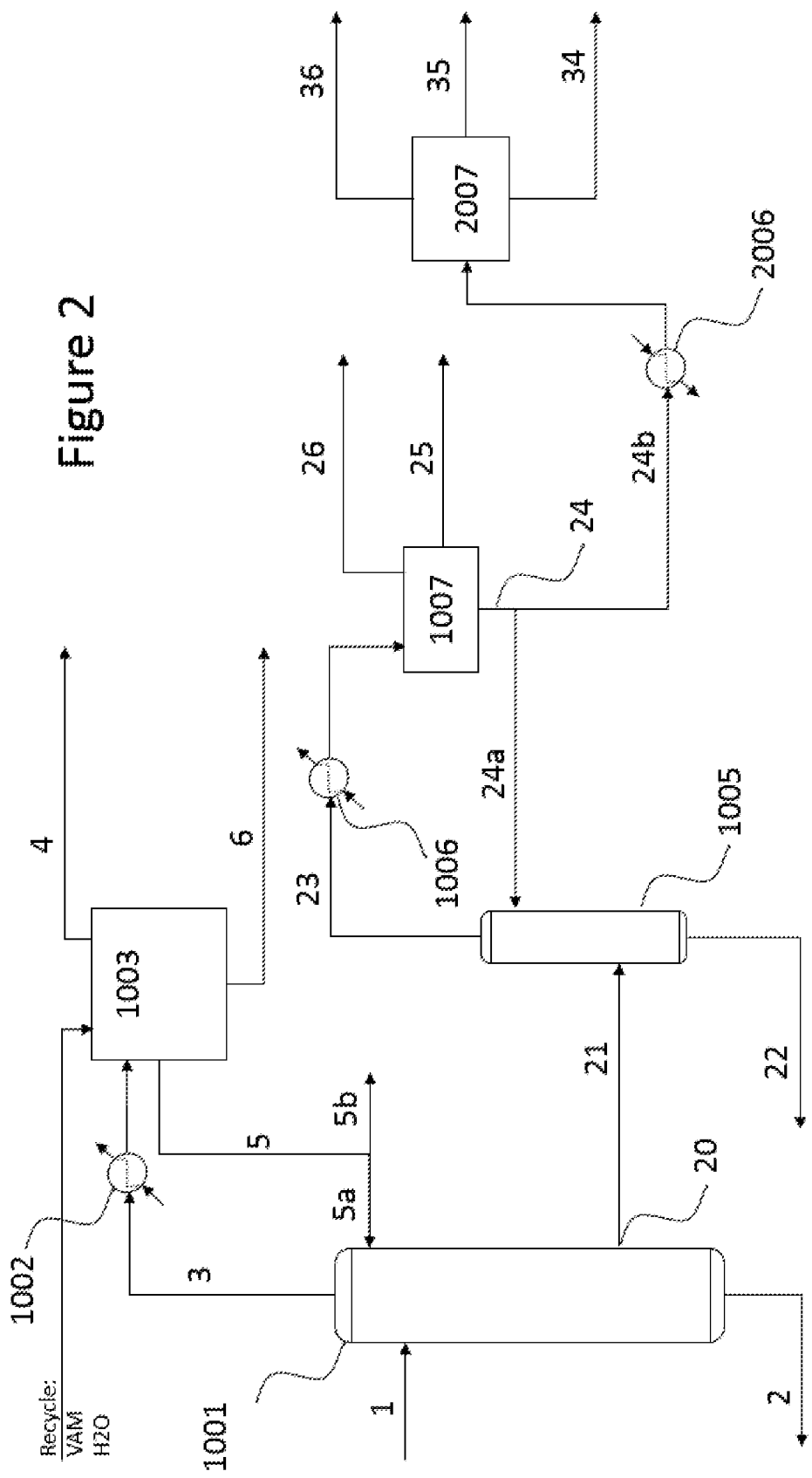
FIG. 2. Schematic of a second embodiment of the disclosed improved crude VAM purification process that allows for further processing of the streams exiting the second distillation tower.

The disclosed improved purification systems are exemplified with respect to FIGS. 1-2. However, these figures are intended to be illustrative only, and not unduly limit the scope of the appended claims. The following description is included to demonstrate embodiments of the appended claims. Those of skill in the art should appreciate that many changes can be made in the specific embodiments which are disclosed and still obtain a like or similar result without departing from the spirit and scope of the disclosure herein.

The product stream exiting an acetoxylation reactor contains unreacted raw material such as ethylene, oxygen, and acetic acid (AA), acetoxylation reaction products, and impurities. Most of the unreacted ethylene, oxygen, and acetic acid (AA) raw materials are removed from the product stream and recycled back to the acetoxylation reactor for further VAM synthesis. The leftover material comprises a crude VAM stream, which contains VAM, AA, water, ETAC, and other impurities. This crude VAM stream is then purified by the purification section of the VAM plant. The presently disclosed systems are directed to improving the purification section of the VAM plant. However, some of the recovered streams from the purification section can be recycled to other areas of the VAM plant, including the acetoxylation reactor and the reaction area of the reactor, to reduce cost of starting material for the acetoxylation and improve water balance for the VAM plant.

FIG. 1 displays one embodiment 1000 of the presently disclosed improved system for purifying a crude VAM stream. This embodiment includes an azeotropic distillation tower 1001, a condenser 1002 and a phase separator 1003 for the overhead product stream 3 exiting tower 1001, a second distillation tower 1005 for processing the side draw stream 21 exiting the azeotropic distillation tower 1001, and a condenser 1006 and phase separator 1007 for the overhead product stream 23 exiting the second distillation tower 1005.

Similar to known purification systems, a crude VAM stream 1 from a vinyl acetate monomer reactor (not shown) is introduced into the azeotropic distillation tower 1001. The crude VAM stream 1 can be fed at a point that is in the middle region of the azeotropic distillation tower 1001. Alternatively, the crude VAM stream 1 can be fed at the middle of the top half of the tower.

The design specifications for the azeotropic distillation tower 1001 will vary by plant, with the number of trays in the azeotropic distillation tower 1001 chosen to balance the equipment cost with the operation cost at that location. Most azeotropic towers will have about 50 to 90 trays, or an equivalent plate count. Alternatively, the azeotropic distillation tower 1001 can have about 60 to 75 trays, or an equivalent plate count. Thus, an azeotropic distillation tower 1001 having 69 total trays (labeled from top to bottom) may have a crude VAM stream inlet at about the thirteenth tray. Alternatively, the inlet may be located between the tenth and eighteenth tray.

During distillation, three streams of distillation products are removed from the azeotropic distillation tower 1001: a bottom product stream 2 that is predominantly AA and water; an overhead, or top, product stream 3 that is predominantly a VAM/water azeotropic mixture; and a side product stream 21 that is enriched in ETAC, but also comprising VAM, AA and water. The operating pressure and temperature of the azeotropic distillation tower 1001 is set to achieve the desired split of distillation products with minimal ETAC in the overhead product.

The operating pressure of the azeotropic distillation tower 1001 is controlled by the pressure of the phase separator 1003 for the predominantly VAM/water overhead product. The pressure of the phase separator 1003 is set at near atmospheric pressure, which correlates to near atmospheric pressure in the azeotropic distillation tower 1001. Alternatively, the set pressure of the phase separator 1003 is maintained between about 1 to 7 psig (about 1 and 1.5 bars of absolute pressure). Another alternative is to maintain the set pressure so that the newly added ETAC tower condenser 1007 can operate at about 5 psig (about 1.4 bars).

The operating temperature of the azeotropic distillation tower 1001 at its top is set by the selected pressure (or pressure range) corresponding to an overhead product stream 3 content of predominantly water and VAM with trace amounts of ETAC in a range of 0.005 to less than 0.02 wt. % or a range of 0.005 to 0.012 wt. % or a range of 0.01 to less than 0.02 wt. % or from 0.008 to 0.015 wt. %. This operating temperature is between about 50 and 80° C., or between about 64 to 72° C. or about 68° C.

A successful azeotropic distillation in tower 1001 will have an overhead product stream with an azeotropic ratio of VAM to water of about 7.5-8.5 wt. % VAM (by weight of water) in the selected operating pressure range. Such azeotropic ratio was previously achieved by co-feeding a water stream with the crude VAM stream in e.g. U.S. Pat. Nos. 4,934,519 and 6,228,226. In the present system, an optional separate stream of water (not shown in FIG. 1) can be co-fed with the crude VAM stream 1 to aid in reaching this ratio.

The VAM/water ratio can be maintained without the need for an extra water stream because water is one of the main byproducts in the ethylene acetoxylation step, and an addition of water is utilized to recover VAM and AA from the reactor vapor effluent. As such, an extra inlet for a water stream to the azeotropic distillation tower 1001 is considered optional in the present system.

The side draw 20 on the azeotropic distillation tower 1001 is an exit for an ETAC enriched side stream 21. The position of the side draw 20 is selected such that the bottom product stream 2 from the azeotropic distillation tower 1001 has a constant amount of water in the range of about 4 and 15 wt. %. Alternatively, the position of the side draw 20 is selected such that the bottom product stream 2 from the azeotropic distillation tower 1001 has a constant amount of water in the range of 4 to 7 wt. %, or 9 and 11 wt. % or 12 to 15%. This placement not only causes the side draw stream 21 to be in the vapor phase, but also increases the ratio of ETAC to VAM in the side draw stream 21, resulting in a decrease in ETAC exiting the azeotropic distillation tower 1001 as an impurity in the overhead stream 3.

The bottom product stream 2 from the azeotropic distillation tower 1001 has a constant amount of water in the range of 4 and 15 wt. %, as well as about or greater than 85% AA, with the remainder of bottom stream 2 being minor impurities that boil at a higher temperature than AA. This bottom product stream 2 can be returned to the VAM reactor for use in producing additional VAM. Alternatively, the bottom product stream 2 can be used in scrubbing and condensing the acetoxylation reactor effluent vapor. The ability to reuse the bottom product stream 2 in various areas of the VAM production process allows for control of the overall water balance for the VAM plant.

The overhead vapor product stream 3 removed from the top of the azeotropic distillation tower 1001 is predominantly water and VAM with trace amounts of ETAC (0.005 to less than 0.02 wt. %, or 0.005 to 0.012 wt. %, or 0.01 to less than 0.02 wt. %, or 0.008 to 0.015 wt. %). This overhead product stream is further condensed in a condenser 1002 and phase separated in the phase separator (e.g. decanter) 1003.

The condenser 1002 can be a heat exchanger type of condenser. These types of condensers use cooling water or fanned air cooling to maintain operating temperatures. As such, the condenser maintains a temperature between 35-60° C. to condense the overhead stream 3, and optional recycle streams. Lower condenser temperatures could be achieved if condensers cooled by e.g. refrigerants were employed.

The phase separator 1003 separates the condensed stream(s) from the overhead product stream 3 into a vapor phase 4, a liquid organic phase 5, and a liquid aqueous phase 6. Any phase separator can be used; however, a decanter is the customary type of phase separator in VAM purification systems. To obtain the three different streams, the phase separator is operated at the same temperatures as the outlet of the condenser 1002 and the same pressures as the azeotropic distillation tower 1001.

The vapor phase 4 contains VAM, water, and incondensable gases such as ethylene and nitrogen. This vapor phase can undergo cooling, chilling or scrubbing steps, with the uncondensed gas being partially recycled to an upstream reaction area and partially purged for disposal as a fuel stream (e.g., for steam generation) or flare stream.

The liquid aqueous phase 6 exiting the phase separator 1003 contains water and VAM. This aqueous stream is further processed to produce a water stream that will be sent to water treatment facilities, and a VAM rich stream that will be combined with other VAM streams for product finishing downstream.

The liquid organic phase 5 contains VAM and water. As shown in FIG. 1, a portion of the liquid organic phase 5 is recycled into the azeotropic distillation tower 1001 as a reflux stream 5a, with the rest being a VAM rich stream 5b. In this process, the proportion of the VAM recycled in reflux stream 5a is regulated such that the desired water content at the bottom of the azeotropic tower 1001 is consistently maintained in the range from about 4 to about 15% by weight. A reflux ratio (ratio of stream 5a to stream 5b) can be in the range of from 2.0 to 4.5. Alternatively, the reflux ratio can be between about 2.5 and about 3.5.

At this point in the purification process, the VAM rich stream 5b still contains trace amounts of ethyl acetate. Due to similar boiling behavior, it is both costly and operation intensive to remove ethyl acetate from this VAM stream, especially if this takes place in a separate distillation step. As such, methods for reducing the amount of ETAC in the VAM stream 5b are employed. These methods include collecting an ethyl acetate-enriched liquid side stream near the bottom of the tower, below the crude VAM feed tray, to concentrate the ETAC. This, in turn, reduces the amount of ETAC that exits within the overhead stream to about 100 to 500 ppm by weight of ETAC. The ETAC-enriched liquid side stream can contain up to 15% by weight of ETAC with varying amounts of water, VAM, and AA. As an illustration, the liquid stream can have about 3.2 wt. % of ETAC, 11.5% VAM, 13.5% water, and 71% of AA. Instead of trying to separate out the water and AA, the liquid side draw stream is directly disposed of by e.g. combustion, which can be costly due to the presence of water and AA.

The presently disclosed systems improve upon the known purification system of the crude VAM stream by moving the side draw point 20 to a location on the azeotropic distillation tower 1001 that maintains a constant water concentration in the bottom product stream 2 of about 4 to about 15 wt. %. At this location, the side stream is a vapor, and the presently disclosed system adds a second distillation tower 1005 for processing this side draw vapor stream. These changes aid in separating out more of the useful components that can be recycled into both the reaction and purification stages of the VAM plant from the side stream and, serve to balance overall plant water usage while maintaining minimal amount of ETAC being recycled back into the VAM production process.

As mentioned above, the side draw 20 is moved to a location on the azeotropic distillation tower 1001 where the bottom product stream 2 has a constant amount of water in the range of 4 to 15 wt. %. This placement of the side draw allows for a vapor based side stream 21 having a larger ratio of ETAC to VAM than the previously used liquid side draw. By having a more ETAC-enriched vapor stream, a minimal draw rate is needed to remove the desired amount of ETAC from the crude VAM distillation. This reduces the amount of coexisting VAM that cannot be economically recovered in the side draw vapor stream 21.

The second distillation tower 1005, also referred to as the ETAC tower, has an inlet about a third of the way up from the bottom to receive the vapor side stream 21 exiting the azeotropic distillation tower 1001. The ETAC tower 1005 is smaller in diameter than the azeotropic distillation tower 1001, and can have about 25 to 60 trays, or equivalent height if packings are used. Alternatively, the ETAC tower can have about 30 to 50 trays or equivalent packing. In yet another alternative, about 45 trays or equivalent packing may be a more economically feasible tower.

As with the azeotropic distillation tower 1001, the pressure in the ETAC tower 1005 is controlled by its phase separator 1007. The vapor side stream 21 feeds into the ETAC tower 1005 under the same pressure at the side draw location 20 in the azeotropic distillation tower 1001. Thus, the feed tray pressure of the ETAC tower 1005 is below the pressure of the side draw tray in the azeotropic tower 1001. To maintain this lower pressure at the feed tray, the ETAC tower phase separator 1007 is operated at pressures near atmospheric. Alternatively, the ETAC tower phase separator 1007 is operated at pressures between about 2 to about 5 psig or about 2 to about 3 psig or about 4 to about 5 psig.

The overhead condensing temperature in the ETAC tower condenser 1006 can be at the highest temperature that satisfies the need for a sufficient water rich flow from the ETAC tower phase separator 1007 or the lowest temperature that the condensing coolant reasonably in ETAC tower condenser 1006 allows. As with condenser 1002, the coolant used in the ETAC tower condenser 1006 can be cooling water, ambient air or cold stream(s), resulting in an operational temperature between about 35 to about 60° C. If lower temperatures than about 35° C. are desired, then refrigerants can be employed to reduce the operating temperatures of the ETAC tower condenser 1006.

Similar to the azeotropic distillation tower 1001 setup, the overhead vapor product stream 23 exiting the ETAC tower 1005 is condensed in the ETAC tower condenser 1006 before being fed to the ETAC tower phase separator 1007. The temperature at the exit of the condenser 1006 affects the content and the flow rates of the various streams exiting the phase separator 1007. As such, this temperature can be optimized by the operator based on the end use, or disposal, of the streams exiting the phase separator 1007 and the downstream devices (e.g., valves, pipes, additional equipment) installed. At temperatures above 78° C., only two streams exit the phase separator 1007: an incondensable gas stream 26 and an aqueous stream 24. At temperatures between about 35° C. to about 78° C., three streams will exit the phase separator 1007: an incondensable gas stream 26, an aqueous stream 24, and an organic stream 25. Regardless of the condenser temperature, the aqueous stream 24 will always be further split into a reflux stream 24a and a water product stream 24b.

Tables 1 and 2 illustrate the advantages of optimizing the operating temperature of the condenser 1006 to control the number streams exiting the phase separator 1007, and their relative compositions, which will affect the end use of the streams. In this example, the VAM purification process shown in FIG. 1 is used, and the pressure of the azeotropic distillation tower 1001 side draw 21 is 9.5 psig (1.6 bars).

Table 1 displays the compositions for the various streams involved in the ETAC distillation for a condensing temperature of 35° C. In temperature ranges between about 35 to about 78° C., the incondensable gas stream 26 has a lower moisture content (2% versus 50.6% at 104° C.), which makes it suitable for use as fuels that can be easily combusted for, e.g., steam generation or flaring. The 'optional' organic stream 25 has no use as a recycle stream in the VAM process, but its high organic content will also make it suitable as fuel for combustion. The mass flow of the reflux stream 24a being recycled to the ETAC tower 1005 is selected to allow for greater than 99% of the AA that was present in side vapor product stream 21 to exit with the bottom product stream 22 of the ETAC tower 1005. The remaining portion of the aqueous stream will form water product stream 24b.

The water product stream 24b is produced in a higher quantity at the lower condenser temperature range, with a mass flow of about 536 kg. This higher mass flow is shown in Table 1, when compared to the mass flow of 24b in Table 2. Because of the cooler condensing temperatures, water product stream 24b will contain 3-4 wt. % ETAC, rendering the water product stream 24b less desirable as a recycle stream to the VAM production process. As such, it will likely be disposed to waste water treatment facilities at battery limit instead of being recycled to maintain the water balance of the plant.

As the condensing temperatures increase, the organic stream 25 decreases until it disappears, while the compositions of streams 24 and 26 change to include the components in the organic stream 25. Table 2 displays the streams and their compositions at a condensing temperature of 104° C. At this high condensing temperature, only two streams exit the ETAC tower phase separator 1007: an incondensable gas stream 26 and an aqueous stream 24. The organic stream 25 has a mass flow of 0 at 104° C., which means there is one less stream to manage and less equipment is needed.

At this higher condensing temperature, the incondensable gas stream 26 has a high moisture content and a large amount of ETAC (28.2% as compared to 16.8% at 35° C.). The high moisture content makes stream 26 a less energy efficient option for use as a fuel gas for combustion. As such, stream 26 is likely to be incinerated.

The increase in moisture and ETAC in stream 26 also reduces the mass flow of stream 24, as seen by the decrease in mass flow of stream 24b in Table 2. This results in the water product stream 24b being greater than 99% pure water, with only about 0.3% of ETAC. The decrease in the flow of stream 24b affects the water balance of the VAM production process, thus the highly pure stream 24b produced at a condensing temperature of 104° C. is likely to be recycled to the VAM production process instead of disposed to waste water treatment facilities at battery limit.

TABLE 1

Concentration of streams when condensed at 35° C.

| Stream    |        | 21    | 22    | 24b   | 25    | 26    |
|-----------|--------|-------|-------|-------|-------|-------|
| mass flow | kg/hr  | 2200  | 1439  | 536   | 223   | 2     |
| Light     | wt. %  | 0.1%  | 0.0%  | 0.0%  | 0.0%  | 64.7% |
| AA        | wt. %  | 63.3% | 96.8% | 0.1%  | 0.0%  | 0.0%  |
| Water     | wt. %  | 25.4% | 3.2%  | 94.3% | 3.6%  | 2.0%  |
| VAM       | wt. %  | 4.6%  | 0.0%  | 1.7%  | 41.5% | 16.0% |
| ETAC      | wt. %  | 6.4%  | 0.0%  | 3.7%  | 54.2% | 16.8% |
| Heavy     | wt. %  | 0.1%  | 0.0%  | 0.2%  | 0.6%  | 0.4%  |

TABLE 2

Concentration of streams when condensed at 104° C.

| Stream    |        | 21    | 22    | 24b   | 25 | 26    |
|-----------|--------|-------|-------|-------|----|-------|
| mass flow | kg/hr  | 2200  | 1439  | 264   | 0  | 497   |
| Light     | wt. %  | 0.1%  | 0.0%  | 0.0%  | —  | 0.3%  |
| AA        | wt. %  | 63.3% | 96.8% | 0.1%  | —  | 0.0%  |
| Water     | wt. %  | 25.4% | 3.2%  | 99.2% | —  | 50.6% |
| VAM       | wt. %  | 4.6%  | 0.0%  | 0.3%  | —  | 20.4% |
| ETAC      | wt. %  | 6.4%  | 0.0%  | 0.3%  | —  | 28.2% |
| Heavy     | wt. %  | 0.1%  | 0.0%  | 0.0%  | —  | 0.5%  |

FIG. 2 displays another improved crude VAM purification system that includes additional purification steps for the overhead stream exiting the ETAC distillation tower. The additional steps will allow for higher recovery of water with improved purity (i.e. less ETAC) for reuse or for disposal without excessive water treatment.

As shown previously in FIG. 1, the overhead stream exiting the ETAC distillation tower is condensed and separated into a vapor stream 26, an organic liquid stream 25 (at low condensing temperatures less than about 78° C.), and a net aqueous stream 24b. The improved system in FIG. 2 provides a flash heater 2006 and a second phase separator 2007 to purify the aqueous stream 24b exiting the phase separator 1007. This is similar to the high condensing temperatures used in condenser 1006. Here, the flash heater 2006 applies heat to stream 24b, which is then separated by phase separator 2007 to form an aqueous only stream 34 and a vapor stream 36. Stream 35 in FIG. 2 is for comparison purposes only as a third stream is not produced.

Table 3 displays stream 24b from Table 1 (condensing temperature of 1007 is 35° C.) after it has been treated with the additional purification steps and the relative concentrations of each stream. When the phase separator 1007 is operated at 35° C., and the exiting aqueous stream 24b is heated to 104° C. by flash heater 2006, stream 34 exiting separator 2007 contains about 0.3% ETAC by weight as compared to 3.7% by weight contained in the stream 24b. The amount of water has also increased from 94.3% to 99.4%, meaning stream 34 is a purer water stream than 24b. The mass flow of stream 34 is about 90% of the mass flow for 24b.

TABLE 3

Concentration of streams on the separator 2007 at 104° C.

| Stream | | 24b* | 34 | 35 | 36 |
|---|---|---|---|---|---|
| mass flow | kg/hr | 536 | 469 | 0 | 68 |
| Light | wt. % | 0.0% | 0.0% | — | 0.1% |
| AA | wt. % | 0.1% | 0.1% | — | 0.0% |
| Water | wt. % | 94.3% | 99.4% | — | 58.8% |
| VAM | wt. % | 1.7% | 0.2% | — | 12.5% |
| ETAC | wt. % | 3.7% | 0.3% | — | 27.3% |
| Heavy | wt. % | 0.2% | 0.0% | — | 1.1% |

*The stream 24b is the same as that in TABLE 1.

As shown in TABLE 3, stream 34 is predominantly water at about the same water purity as, but much higher flow rate than, the stream 24b in TABLE 2. Further as compared to TABLE 1, the aqueous stream 34 is nearly 90% of the aqueous stream 24b in flow rate yet at much higher purity in water or much lower in ETAC content. This addition would be helpful to produce a cleaner, more pure water stream (99.4% vs. 94.3%).

The above examples show that it is possible to modify the VAM purification system to improve the removal of ETAC from a crude VAM stream in a cost-effective manner. While some initial capital investment is necessary for the additional distillation tower and moving the side stream draw location, the energy consumption and water use in the purification section on the VAM plant is drastically lower when compared to a process that separates ETAC and VAM downstream from the purification section. This additional distillation not only reduces the amount of ETAC that would have remained in the VAM product stream (streams 5b and 6), it also increases the recovery of water for recycle and/or disposal at lower cost. In some embodiments, the settings on the condenser and phase separator for the ETAC distillation tower can also result in purer (>99%) water streams for use in other parts of the plant. The improved systems described herein further provide flexibilities in purposing the recovered ETAC containing organic streams with options such as flare, fuels, and offsite disposal. This leads to reduced overall costs in VAM production.

The following are incorporated by reference in their entirety.
U.S. Pat. No. 4,934,519
U.S. Pat. No. 6,228,226

What is claimed is:

1. A method for purifying a crude liquid vinyl acetate feed stream comprising:
    a) feeding the crude liquid vinyl acetate feed stream from a vinyl acetate monomer reactor into a first distillation tower, wherein the crude liquid vinyl acetate feed stream comprises vinyl acetate monomer, acetic acid, water, and ethyl acetate, and wherein the first distillation tower comprises a top of the first distillation tower and a bottom of the first distillation tower;
    b) distilling the crude liquid vinyl acetate feed stream;
    c) removing a first vapor product from the top of the first distillation tower, wherein the first vapor product is predominantly a water and vinyl acetate monomer azeotrope mixture;
    d) removing a first liquid product from the bottom of the first distillation tower, wherein the first liquid product comprises water and acetic acid;
    e) removing a first vapor side stream from the first distillation tower, wherein the first vapor side stream comprises acetic acid, water, vinyl acetate monomer and ethyl acetate,
    f) feeding the first vapor side stream from the first distillation tower into a second distillation tower;
    g) distilling the first vapor side stream in the second distillation tower, wherein the second distillation tower comprises a top of the second distillation tower and a bottom of the second distillation tower;
    h) removing a second liquid product comprising acetic acid and water from the bottom of the second distillation tower,
    i) removing a second vapor product comprising vinyl acetate monomer, ethyl acetate and the remaining water from the top of the second distillation tower;
    j) condensing the second vapor product; and
    k) separating the condensed second vapor product into a third vapor stream, a first aqueous stream and an optional organic stream, wherein a first portion of the first aqueous stream is returned to the second distillation tower as reflux and a second portion of the first aqueous stream is sent to a water treatment plant or a reaction area of the vinyl acetate monomer reactor.

2. The method of claim 1, further comprising the steps of:
    l) condensing and separating the first vapor product to form a second aqueous stream and a first vapor phase,
    m) purging the first vapor phase, and
    n) feeding the second aqueous stream to either a water treatment plant or the reaction area of the vinyl acetate monomer reactor.

3. The method of claim 1, wherein the liquid product removed from the bottom of the first distillation tower has a constant water concentration of about 4 to 15 wt. %.

4. The method of claim 1, wherein the first distillation tower contains 50 to 90 trays and is operated under 1 to 5 bars of absolute pressure.

5. The method of claim 1, wherein a feed inlet tray of the first distillation tower is located between a middle section of the first distillation tower and the top of the first distillation tower.

6. The method of claim 1, wherein the condensing of the second vapor product stream is in a temperature range of about 35 to about 105° C.

7. The method of claim 1, wherein the optional organic stream from the condensed second vapor product is present when the condensing occurs in a temperature range of about 35 to about 78° C.

* * * * *